United States Patent [19]
Kato et al.

[11] 3,966,776
[45] June 29, 1976

[54] PROCESS FOR PREPARING PARABENZOQUINONES
[75] Inventors: Takashi Kato, Yokohama; Toru Yamanaka, Kamakura; Akira Komatsu, Tokyo, all of Japan
[73] Assignee: Takasago Perfumery Co., Ltd., Tokyo, Japan
[22] Filed: Sept. 10, 1974
[21] Appl. No.: 504,796

Related U.S. Application Data
[63] Continuation-in-part of Ser. No. 339,787, March 9, 1973, abandoned.

[52] U.S. Cl............................ 260/396 R; 260/369
[51] Int. Cl.$^2$.................. C07C 49/64; C07C 49/66; C07C 49/68
[58] Field of Search............ 260/396 R, 396 N, 369

[56] References Cited
UNITED STATES PATENTS

| | | | |
|---|---|---|---|
| 3,455,880 | 7/1969 | Kobayashi et al. | 260/396 R |
| 3,658,852 | 4/1972 | Schuster et al. | 260/396 R |

Primary Examiner—Vivian Garner
Attorney, Agent, or Firm—Sughrue, Rothwell, Mion, Zinn & Macpeak

[57] ABSTRACT

A process for preparing parabenzoquinones which comprises oxidizing alkylphenols with oxygen or an oxygen-containing gas in the presence of cobalt di-(salcylal)-3,3′-diimino-di-n-propylamine derivatives and an amine is disclosed.

13 Claims, No Drawings

PROCESS FOR PREPARING PARABENZOQUINONES

CROSS REFERENCE TO RELATED APPLICATION

The present application is a continuation-in-part of U.S. application Ser. No. 339,787 filed Mar. 9, 1973, now abandoned, in the names of Takashi Kato et al. and entitled "Process for Preparing Parabenzoquinones".

BACKGROUND OF THE INVENTION

1. Field of the Invention

This invention relates to a process for preparing parabenzoquinones.

2. Description of the Prior Art

The process which has hitherto been employed for preparing parabenzoquinones by oxidizing alkylphenols includes an oxidization using salcomine [bis(salcylidene)-ethylene-diimino cobalt complex (II)] [Rec. Trav. Chim., vol 86, pp 520 (1967)]. This conventional complex exhibits a low activity for the conversion of phenols to quinones, but the most unfavorable disadvantage of the cobalt complex (II) in industrial use is that a large amount of polymers such as polyphenylether and the like are by-produced during oxidization (as is common in a direct liquid phase oxidization of alkylphenols with air in the presence of a catalyst) and, therefore, recovery of the catalyst is impossible due to the presence of these polymers. Further, the cobalt complex (II) is of poor solubility and the formation of polymers increases when the oxidization is carried out at a sufficiently high temperature to dissolve the cobalt complex (II) in a solvent. Moreover, the cobalt complex (II) lacks selectivity so that oxidization is conducted even on an alkylphenol having an alkyl substituent at the para-position as well as well as other alkylphenols.

In the light of the disadvantages described above, the process using the cobalt complex (II) has been recognized as unsuitable for industrial use for the production of parabenzoquinones.

SUMMARY OF THE INVENTION

The primary object of the present invention is, therefore, to provide a novel process for preparing parabenzoquinones by selectively oxidizing alkylphenols which do not have an alkyl substituent at the paraposition with respect to the —OH group.

Another object of the present invention is to provide a process which will be highly advantageous in industrial use for the production of parabenzoquinones, useful intermediates for the synthesis of trimethylhydroquinone and the like which are important starting materials in organic syntheses for anti-oxidants, photographic developers, dyes, vitamin E (see P. Karrer et al: Helv. Chim. Acta 21, 520 2243 2357 (1938) and Coenzyme Q (R. A. Morton et al: Helv. Chim. Acta 41 2243, 2357 (1958)).

The present invention involves a process of oxidizing alkylphenols with oxygen or oxygen-containing gas in the presence of cobalt di-(salcylal)-3,-3 '-diimino-di-n-propylamine derivatives (I) and one or more amines to prepare the corresponding parabenzoquinones.

DETAILED DESCRIPTION OF THE INVENTION

The cobalt complex (I) used as a catalyst in the present invention includes those having nucleus substituents such as an alkyl and alkoxy group having 1 to 3 carbon atoms, a halogen and a nitro group at the 3- and 5-position of the salcylaldehyde moiety thereof, with the amine moiety being a triamine having a 3,3'-diamino-di-n-propyamine structure, and can be represented by the formula:

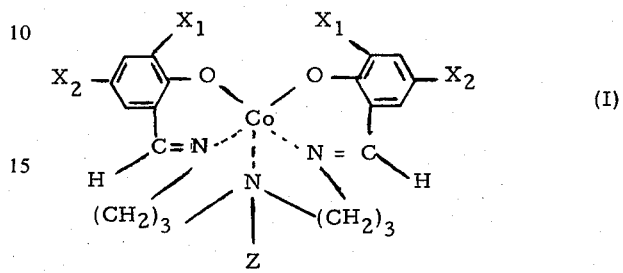

wherein $X_1$ and $X_2$ each represents a hydrogen atom, a halogen atom, an alkyl and alkoxy group having 1 to 3 carbon atoms or a nitro group; and Z represents a hydrogen atom or an alkyl group having 1 to 3 carbon atoms.

This cobalt complex (I) can be prepared by known methods [see R. H. Bailes, M. Calvin: J. Am. Chem. Soc. vol 69, pp 1886-1893 (1947)].

This cobalt complex (I) is used in a homogeneous system in the oxidization reaction between alkylphenols and oxygen or an oxygen-containing gas such as air. The amount of the cobalt complex (I) to be used is not limited to any specific range, but usually a small amount of the complex will be sufficient, particularly, 1/1000 to 1/10 mole per 1 mole of alkylphenols being advantageous to give good results.

The above described cobalt complex (I) is superior to that conventionally used (salcomine) in that the cobalt complex (I) does not bring about the formation of polymers such as polyphenylether and also exhibits very high solubility in solvents. Further, the cobalt complex (I) has the excellent advantage that it does not act as a catalyst for the oxidization of an alkylphenol having an alkyl substituent at the 4-position, i.e., only an alkylphenol which does not have an alkyl substituent at the 4-position is selectively and quantitatively oxidized to be converted into the corresponding parabenzoquinone.

The amine used in the present invention includes any primary, secondary or tertiary amine.

However, the ability of amines to coordinate with a cobalt complex is dependent upon the size of the amine molecule. Any amine can be used in the present invention which has one or two nitrogen atoms and which contains up to 15 carbon atoms.

Examples of preferred amines include ammonia (which contains, of course, no carbon atoms), aliphatic amines, N-alkylanilines, pyrrolidines, piperidines, α-aminoalcohols, diamines, guanidines, pyridines, pyrimidines and the like.

The essential feature or limitation on the amines is thus specifically the number of nitrogen atoms (one or two) and the number of carbon atoms (up to and including 15, noting that ammonia is included as having 0 carbon atoms).

Specific examples of such amines are trimethylamine, triethylamine and N-methylpiperidine, quinoline, 2,6-dimethyl-pyridine, morpholine and the like.

Most preferred amines have pKa values between 9–11. While some of the above amines have such a pKa value, not all of such amines do. Amines having a pKa value of 9–11 give optimum reaction results, though the present invention is not limited thereto.

Amines having a pKa value of 9–11 are preferred for the following reason. When an amine is used as a ligand it must substitute with an alkylphenol. In such a case, there is a relationship between the pKa value of the amine and of the alkylphenol. Representative alkylphenol pKa values are as follows:

| Alkylphenol | pKa |
|---|---|
| 2,3-dimethylphenol | 10.37 – 10.54 |
| 2,5-dimethylphenol | 10.18 – 10.60 |
| 2,6-dimethylphenol | 10.5 – 10.63 |
| 2,4,6-trimethylphenol | 10.77 – 10.99 |
| 2,3,5-trimethylphenol | 10.69 |

The pKa value of the amine should not be substantially larger than that of the alkylphenol undergoing reaction. On the other hand, if the pKa value of the amine is substantially smaller than 9, it is difficult to coordinate with an oxygen atom (the activity of oxygen becomes small) and the formation of phenoxy radicals increases, leading to the formation of polymer.

Based upon the above, amines having a pKa value of 9–11 are preferred. However, this is not an absolute restriction on the amines used for the present invention since some of the amines heretofore specifically exemplified have pKa values outside of this range. The amine is used in an amount of one mole per 0.1 to 3 moles of the cobalt complex (I) and the preferred amine ratio is one mole cobalt complex: one mole amine. The amine acts as a ligand of the cobalt complex (I) thereby promoting the reaction, and the amines can be used singly or as mixtures.

Alkylphenols to which the process of the present invention may be applied include monocyclic or polycyclic aromatic phenols, excluding those having an alkyl substituent at the para-position. Preferred alkylphenols processed in accordance with this invention can be shown as follows:

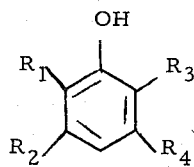

$R_1$, $R_2$, $R_3$ and $R_4$ each can represent hydrogen atom, with at least one of $R_1$ - $R_4$ being an alkyl group, e.g., an alkyl group having 1 to 4 carbon atoms or $R_1$, $R_2$ and $R_3$, $R_4$ form a benzene ring together, for example 2,3-dimethylphenol, 2,5-dimethylphenol, 2,6-dimethylphenol, 2,6-di-t-butylphenol, 2,3,5-trimethylphenol, 1-naphthol and anthranol.

Although rates of oxygen absorption and oxidization of alkylphenols in the presence of the cobalt complex (I) are somewhat lower than those obtained in the presence of salcomine and the rate of oxidization varies in proportion to the oxygen partial pressure, the present process can be carried out under normal pressure with high yields without an extreme increase in the oxygen partial pressure. Up to 5 Kg/cm² of oxygen partial pressure, the greater the pressure the faster the oxidization velocity. Above 5 $Kg/cm^2$ of oxygen partial pressure, the velocity does not increase directly in proportion to the pressure, so such will usually not be used. The cobalt complex (I) exhibits almost no catalytic activity on oxidization at a low temperature and the reaction is advantageously carried out at a temperature higher than 10°C, generally from 10° to 50°C.

The process of the present invention is carried out by dissolving or suspending an alkylphenol, the complex (I) and the amine in any appropriate organic solvent. Hydrocarbon or halogenated hydrocarbon solvents such as chloroform, benzene or the like are generally employed in an amount sufficient to dissolve the reactants. The solvent selected is not critical, so long as it is inert to the reaction. Oxygen or an oxygen-containing gas, e.g., air, is bubbled through the resulting solution or suspension so as to be uniformly contacted with the reactants whereupon the oxygen is advantageously absorbed and the oxidization smoothly proceeds.

Completion of the reaction can be determined by analysis using chromatography and the like. The results obtained, as shown in Examples 1 to 8, indicate that parabenzoquinones are obtained in extremely high yields in the presence of the complex (I) according to the present invention.

Reaction time is not important, and reaction conditions are merely maintained until analysis shows completion. Higher temperatures and/or oxygen partial pressures speed reaction, however.

As is described above in detail, the process according to the present invention is believed to be an excellent invention which makes it possible to obtain parabenzoquinones in high yields by selectively oxidizing alkylphenols with oxygen or an oxygen-containing gas in the presence of a specific catalyst and at least one amine.

The process of the present invention will now be further illustrated by way of examples, but such examples are not to be construed as limiting the present invention. Various changes and modifications can be made therein without departing from the spirit and the scope of the present invention.

Unless otherwise indicated, all percentages in the examples are weight percent, and reaction was at atmospheric pressure.

EXAMPLE 1

3.96 g of cobalt di-(salcylal)-3,3'-diimino -di-n-propylamine (0.1 mole) and 1.01 g of triethylamine (0.01 mole) were dissolved in 100 ml of chloroform and oxygen gas (100 ml/min) was then bubbled into the resulting solution for 5 seconds at a temperature of 10°C to form an oxygen complex. To this was added a solution of 13.6 g of 2,3,5-trimethylphenol (0.1 mole) in 100 ml of chloroform in three portions and oxygen gas (250 ml/min) was again introduced into the solution for a period of 8 hours to complete the reaction. After completion of the reaction, chloroform was distilled off and the residue was steam distilled by introducing steam thereinto. The distillate was extracted with ether and the ether was then distilled off to give 15.0 g of pseudocumoquinone (0.1 mole) having a melting point of 32°C, that is, the yield was quantitative.

Catalysts may be recovered by extracting the residue obtained from the above steam distillation with chloroform.

It is to be noted that the amine addition step (ligand formation) need not be performed as a separate step, and so long as all essential components are present at the time of reaction this is sufficient. No special steps or precautions need be taken for amine addition (ligand formation).

EXAMPLES 2 – 7

The following experiments were carried out according to Example 1, but the cobalt complex was varied as indicated in Table 1. The yield of pseudocumoquinone was the same as that of Example 1.

Table 1

| Example No. | Cobalt complex |
|---|---|
| 2 | Cobalt-di-(3-chlorosalcylal)-3,3'-diimino-di-n-propylamine |
| 3 | Cobalt-di-(5-nitrosalcylal)-3,3'-diimino-di-n-propylamine |
| 4 | Cobalt-di-(3-nitrosalcylal)-3,3'-diimino-di-n-propylamine |
| 5 | Cobalt-di-(5-chlorosalcylal)-3,3'-diimino-di-n-propylamine |
| 6 | Cobalt-di-(3-methoxysalcylal)-3,3'-diimino-di-n-propylamine |
| 7 | Cobalt-di-(salcylal)-3,3'-diimino-di-n-propyl-methylamine |

EXAMPLE 8

12.2 g of 2,5-dimethylphenol (0.1 mole), 1.98 g of cobalt di-(3-methylsalcylal)-3,3'-diimino-di-n-propylamine (0.0005 mole) and 0.5 g of N-methylpiperidine were dissolved in 200 ml of chloroform and then air was bubbled through the resulting solution at 15°C for 10 hours during which time the reaction was completed. After completion of the reaction, the reaction mixture was rendered basic by adding a 2% aqueous solution of sodium hydroxide to decompose peroxides present in the mixture followed by addition of dilute hydrochloric acid to render the solution acidic. The resulting solution was extracted with ether which was then distilled off to obtain 12.1 g of 2,5-dimethyl-parabenzoquinone (0.09 mole).

EXAMPLE 9

0.4 g of cobalt di-(5-methylsalcylal)-3,3'-diimino-di-n-propylamine (0.0001 mole) was dissolved in chloroform. To this was added 0.2 ml of an aqueous solution of 30% trimethylamine (0.0001 mole), which had been dissolved in 20 ml of chloroform, followed by the introduction of oxygen thereinto, but very little oxygen was absorbed. Upon adding a solution of 1.36 g of 2,3,5-trimethylphenol (0.01 mole) in 200 ml of chloroform to the above solution, the absorption of oxygen started, and in 5 hours the theoretical amount of oxygen was absorbed (224 ml). After the reaction was completed, the chloroform was distilled off and the residue was subjected to steam-distillation. The distillate was extracted with ether and the ether was then distilled off to give 1.5 g of pseudocumoquinone, (0.01 mole), that is, the yield was quantitative.

EXAMPLES 10–12

The following examples were carried out in accordance with Example 9 except that different amines were employed.

Table II

| Example No. | Amine (as ligand) | Yield of pseudocumoquinone (wt.%) |
|---|---|---|
| 10 | quinoline | 98 |
| 11 | 2,6-dimethylpyridine | 90 |
| 12 | morpholine | 100 |

EXAMPLES 13–22

In the same manner as described in Example 1, alkylphenols as shown in the following table were oxidized to obtain the corresponding parabenzoquinones in the yield as indicated in the table.

Table III

| Example No. | Alkylphenol | Parabenzoquinone | Yield (wt.%) |
|---|---|---|---|
| 13 | 2,3-dimethylphenol | 2,3-dimethylparabenzoquinone | 98 |
| 14 | 2,5-dimethylphenol | 2,5-dimethylparabenzoquinone | 85 |
| 15 | 2,6-dimethylphenol | 2,6-dimethylparabenzoquinone | 88 |
| 16 | 2,6-di-t-butylphenol | 2,6-di-t-butyl parabenzoquinone | 90 |
| 17 | 2,3,5-trimethylphenol | pseudocumoquinone | quantitatively obtained |
| 18 | 1-naphthol | 1,4-naphthoquinone | 92 |
| 19 | anthranol | anthraquinone | 90 |
| 20 | phenol* | | almost no oxidation |
| 21 | 2,4,5-trimethylphenol* | | " |
| 22 | 2,4,5-trimethylphenol* | | " |

*Comparison

In the above process, on occasion monoalkyl starting phenols require stringent reaction control to susccessfully oxidize the same. Further, the commercial value of the products of such a reaction (where only one of $R_1$, $R_2$, $R_3$ or $R_4$ is alkyl) is relatively low. From the chemical view point, it can thus be said that the present invention is of practical interest for those cases where two, three or all of $R_1$, $R_2$, $R_3$ and $R_4$ are alkyl as defined above, i.e., $C_1$ to $C_4$ alkyl, and at most only two of $R_1$ to $R_4$ are hydrogen.

EXAMPLE 23

0.4 g of cobalt di-(salcylal)-3,3'-diimino-di-n-propylamine (0.0001 mole) was dissolved in 100 ml of toluene. 0.2 ml of a 28% ammonia solution was added thereto and then air was bubbled into the resulting solution for 5 minutes at a temperature of 5°C at a rate of 250 ml/min. After further adding 13.6 g of 2,3,6-trimethylphenol (0.1 mole) thereto, air (250 ml/min)

was bubbled through the resulting solution at 5°C for 10 hours. After the completion of the reaction, toluene was distilled off and the residue was steam distilled by introducing steam thereinto. The distillate was extracted with ether and the ether was then distilled off to give 13 g of 2,3,6-trimethyl-p-benzoquinone (Yield: 87%).

EXAMPLES 24–35

The following examples were carried out in accordance with Example 1 except that different amines were employed.

| Example No. | Amine (as ligand) (0.01 mole) | Yield of pseudocumoquinone (theory %) |
|---|---|---|
| 24 | tributylamine | quantitatively obtained |
| 25 | triamylamine | 46.5 |
| 26* | trihexylamine | 13.3 |
| 27 | pentadecylamine | 48 |
| 28* | hexadecylamine | 15.5 |
| 29 | cyclohexylamine | 80 |
| 30 | benzylamine | 61 |
| 31 | N,N-dimethylaniline | 65 |
| 32 | monoethanolamine | 65 |
| 33 | diethanolamine | 70 |
| 34 | ethylenediamine | 55 |
| 35 | N-methylpyrroline | 75 |

Note: *Comparative Example

While the invention has been described in detail and with reference to specific embodiments thereof, it will be apparent to one skilled in the art that various changes and modifications can be made therein without departing from the spirit and scope thereof.

What is claimed is:

1. A process for preparing a parabenzoquinone which comprises oxidizing an alkylphenol with oxygen or oxygen-containing gas in an inert organic solvent in the presence of a cobalt-di-(salcylal)-3,3'-diimino-di-n-propylamine derivative and an amine selected from the group consisting of ammonia and primary, secondary and tertiary amines having 1 or 2 nitrogen atoms and containing up to and including 15 carbon atoms, wherein:

said derivative is of the formula:

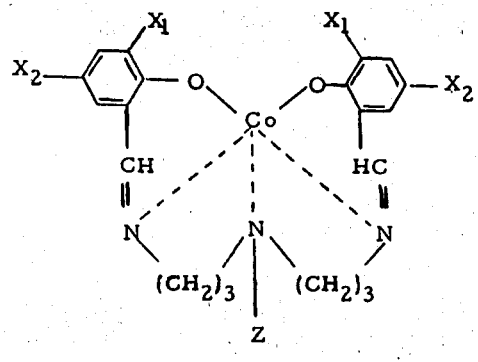

(I)

wherein $X_1$ and $X_2$ each represents a hydrogen atom, a halogen atom, an alkyl or alkoxy group having 1 to 3 carbon atoms or a nitro group; and Z represents a hydrogen atom or an alkyl group having 1 to 3 carbon atoms;

reaction is at 10°C to 50°C; and
the alkylphenol is of the formula:

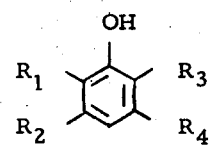

wherein $R_1$, $R_2$, $R_3$ and $R_4$ are hydrogen or a $C_1$–$C_4$ alkyl group, at least 1 of $R_1$–$R_4$ being $C_1$–$C_4$ alkyl group.

2. The process of claim 1 wherein said amine is selected from the group consisting of ammonia, aliphatic amines, N-alkylanilines, pyrrolidines, piperidines, quanidines, pyridines, and pyrimidines.

3. The process of claim 1 where the components are present at the following molar ratios:
cobalt derivative: 1/1000 to 1/10 mole per 1 mole of alkylphenol
amine: one mole per 0.1 to 3 moles of cobalt derivative.

4. The process according to claim 1, wherein said cobalt complex (I) is cobalt-di-(salcylal)-3,3'-diimino-di-n-propylamine or cobalt-di-(salcylal)-3,3'-diimino-di-n-propyl-methylamine.

5. A process according to claim 1, wherein said amine is trimethylamine, triethylamine or N-methylpiperidine.

6. A process according to claim 1, wherein said alkylphenol is 2,3,5-trimethylphenol or 2,5-dimethylphenol.

7. A process according to claim 1, where reaction is at an oxygen partial pressure up to 5 Kg/cm².

8. A process according to claim 1 wherein the organic solvent is a hydrocarbon or halogenated hydrocarbon.

9. A process according to claim 8 where the solvent is chloroform or benzene.

10. A process according to claim 11 wherein the amine is trimethylamine, triethylamine, N-methylpiperidine, quinoline, 2,6-dimethylpyridine or morpholine.

11. A process according to claim 1 where the amine is used in an amount of 1 mol per mol of the cobalt complex.

12. The process of claim 1 wherein said amine is an α-aminoalcohol.

13. The process of claim 1 wherein said amine is a diamine.

* * * * *